United States Patent [19]
Chen et al.

[11] Patent Number: 5,955,641
[45] Date of Patent: Sep. 21, 1999

[54] METHOD OF MAKING DIMETHYLNAPHTHALENES

[75] Inventors: Cong-Yan Chen, Richmond; William L. Schinski, San Rafael; Dennis J. O'Rear, Petaluma; Thomas V. Harris, Benecia, all of Calif.

[73] Assignee: Chevron Chemical Company LLC, San Francisco, Calif.

[21] Appl. No.: 09/086,295

[22] Filed: May 28, 1998

Related U.S. Application Data

[60] Provisional application No. 60/078,222, Mar. 16, 1998.

[51] Int. Cl.⁶ ............... C07C 1/00; C07C 2/70; C07C 2/68; C10G 35/06
[52] U.S. Cl. ............ 585/320; 585/323; 585/459; 585/466; 585/467; 208/135; 208/137
[58] Field of Search .................. 585/320, 323, 585/459, 466, 467; 208/135, 137, 138, 141

[56] References Cited

U.S. PATENT DOCUMENTS

| | | | |
|---|---|---|---|
| 3,109,036 | 10/1963 | Suld et al. | 260/668 |
| 3,541,175 | 11/1970 | Hedge | 260/674 |
| 3,594,436 | 7/1971 | Hedge et al. | 260/674 N |
| 3,668,267 | 6/1972 | Hedge | 260/674 SA |
| 3,725,490 | 4/1973 | Nagahama et al. | 260/674 N |
| 3,803,253 | 4/1974 | Suld et al. | 260/668 A |
| 3,806,552 | 4/1974 | Oka et al. | 260/668 A |
| 3,839,479 | 10/1974 | Hedge | 260/674 N |
| 3,851,002 | 11/1974 | Oka et al. | 260/668 A |
| 3,855,328 | 12/1974 | Hedge | 260/668 A |
| 3,888,938 | 6/1975 | Ogasawara et al. | 260/668 A |
| 3,890,403 | 6/1975 | Shimada et al. | 260/674 N |
| 3,928,482 | 12/1975 | Hedge et al. | 260/668 F |
| 4,556,751 | 12/1985 | Maki et al. | 585/481 |
| 4,777,312 | 10/1988 | Bakas et al. | 585/481 |
| 4,791,235 | 12/1988 | Maki et al. | 585/806 |
| 4,835,334 | 5/1989 | Hobbs et al. | 585/831 |
| 4,962,260 | 10/1990 | Sikkenga et al. | 585/481 |
| 5,004,853 | 4/1991 | Barger et al. | 585/481 |
| 5,043,501 | 8/1991 | Del Rossi et al. | 585/323 |
| 5,059,742 | 10/1991 | Miyashi et al. | 585/860 |
| 5,064,630 | 11/1991 | Verduijn et al. | 423/328 |
| 5,146,040 | 9/1992 | Verduijn et al. | 585/825 |
| 5,220,098 | 6/1993 | Nakamura et al. | 585/812 |
| 5,254,769 | 10/1993 | Takagawa et al. | 585/477 |
| 5,268,523 | 12/1993 | Fellmann et al. | 585/446 |
| 5,481,055 | 1/1996 | Takagawa et al. | 585/481 |
| 5,495,060 | 2/1996 | Takagawa et al. | 585/481 |
| 5,510,563 | 4/1996 | Smith et al. | 585/812 |

OTHER PUBLICATIONS

Ferino et al., "Isomerization of dimethylnaphthalenes Over Zeolites", React. Kinet. Catal. Lett., vol. 58, No. 2, pp. 307–314 (1996).

U.S. application No. 08/892,508, filed Jul. 14, 1997, entitled "Method of Making 2,6–Dimethylnaphthalene from Other Dimethylnaphthalene Isomers and From Dimethyltetralins/Dimethyldecalins with a Methyl Group on Each Ring", Donald S. Santilli et al.

U.S. application No. 09/000,858, filed Dec. 30, 1997, entitled "Method for Producing 2,6–DMN from Mixed Dimethylnaphthalenes by Crystallization, Adsorption and Isomerization", Curtis L. Munson et al.

Primary Examiner—Glenn Caldarola
Assistant Examiner—In Suk Bullock
Attorney, Agent, or Firm—Timothy J. Hadlock

[57] ABSTRACT

The method of the invention includes making dimethyinaphthalenes by first contacting, in an alkylation zone, at alkylation conditions, a toluene-containing stream with a pentene-containing stream in the presence of an acid alkylation catalyst. At least a portion of the toluene and pentenes react to form pentyltoluenes. At least a portion of the pentyltoluenes is then contacting in a reforming zone with reforming catalyst, at reforming conditions. At least a portion of the pentyltoluenes is converted to dimethylnaphthalenes.

50 Claims, 3 Drawing Sheets

METHOD OF MAKING DIMETHYLNAPHTHALENES

CROSS-REFERENCE TO RELATED APPLICATIONS

This application claims priority from U.S. Provisional Application Ser. No. 60/078,222, filed Mar. 16, 1998.

FIELD OF THE INVENTION

The invention relates to a method of making dimethylnaphthalenes.

BACKGROUND OF THE INVENTION

Dimethylnaphthalenes ("DMN") are valuable for use in a variety of chemical manufacturing processes. 2,6-dimethylnaphthalene ("2,6-DMN"), e.g., is particularly valuable. 2,6-DMN is a precursor for the manufacture of 2,6-naphthalene dicarboxylic acid ("2,6-NDA") and 2,6-naphthalene dicarboxylate ("2,6-NDC"). 2,6-NDA and 2,6-NDC are monomers either of which, when combined with ethylene glycol, reacts to make polyethylene naphthalate ("PEN"), a polyester which provides superior strength and heat resistance compared to polyethylene terephthalate ("PET") in applications such as films (e.g., photographic film), fibers, containers and molded parts and has, therefore, unique commercial advantages. Thus, there has been recently worldwide increasing interest in the production of 2,6-DMN, 2,6-NDA and 2,6-NDC.

Naturally, there is an interest in having an economical and efficient process for their manufacture. 2,6-NDA and 2,6-NDC production is similar to that of terephthalic acid in that a 2,6-dialkylnaphthalene, e.g., 2,6-DMN, is oxidized to the corresponding acid by using well established methods. Thus, the challenge lies in the manufacture of dialkylnaphthalenes (especially DMN's) from which the 2,6-dialkylnaphthalenes are produced then via a variety of methods including isomerization and separations. As a result, it is highly desirable to find an economical way to manufacture DMN's, particularly 2,6-dialkylnaphthalenes, and especially 2,6-DMN.

Several conventional methods for producing 2,6-naphthalene dicarboxylic acid precursors are known. These methods, which all lead to production of DMN's, can be grouped as follows: (1) alkenylation/cyclization/dehydrogenation, starting with a monocyclic aromatic and a diolefin, (2) reforming/recovery from kerosene fractions, (3) recovery from cycle oil produced in fluid catalytic cracking (FCC) operations, and (4) transalkylation of naphthalene with polyalkylbenzenes. In addition, alkylation (e.g., methylation or propylation) of naphthalene is also an alternative method to produce dialkylnaphthalenes.

In regards to the first category of methods listed above, U.S. Pat. No. 4,990,717 discloses a method for production of a monoalkenylated aromatic via base-catalyzed reactions. The reactions are performed by reacting an alkylbenzene (e.g., ortho-xylene or para-xylene) with a $C_4$ or $C_5$ conjugated diene over a fixed bed of supported alkali metal catalyst. Similar reactions using a dispersed alkali metal catalyst are also disclosed in a number of even earlier patents such as U.S. Pat. Nos. 3,953,535, 3,954,895 and 3,954,896. Another known process teaches a method for producing pentyltoluenes. This method is disclosed in U.S. Pat. No. 3,931,348 (the '348patent). The '348 patent teaches producing DMN's from a pentyltoluene/pentenyltoluene obtained from addition of p-xylene and butene or butadiene.

These various approaches are each aimed at making pentyltoluenes/pentenyltoluenes which can be then selectively converted. The conversion is via a subsequent cyclization and dehydrogenation step to DMN's which belong to the same DMN triad as 2,6-DMN (vide infra for the DMN triads). Discovery of an alternative method to these known methods for making DMN's is highly desirable. These known methods are expensive because they involve the relatively expensive starting materials, the relatively expensive base catalysts and the restrictions on manufacturing those DMN precursors which can be selectively converted to the DMN's belonging to the 2,6-DMN triad.

Other methods for the two-stage process of cyclization and dehydrogenation reactions are disclosed, for example, in U.S. Pat. Nos. 5,012,024, 5,030,781, 5,073,670 and 5,118,892. In those references, cyclization of monoalkenylated toluene is accomplished over a zeolite catalyst containing platinum and copper to a dimethyltetralin such as 1,5-dimethyltetralin. These references teach that dehydrogenation of dimethyltetralins typically takes place over a platinum/rhenium catalyst supported on alumina. This method is also undesirable since it involves at least two distinct steps and is relatively expensive.

Yet another known process teaches alkylating toluene with 1-pentene. This method is taught in U.S. Pat. No. 5,043,501. The resulting alkylate is then catalytically dehydrocyclized by contacting with a zeolite L to produce DMN's. This process, however, has many drawbacks. Pure 1-pentene streams are unduly expensive and the yield of DMN's with zeolite L is very poor.

A combined cyclization and dehydrogenation operation is taught in U.S. Pat. No. 5,068,480. The process comprises subjecting 2-methyl-1-(p-tolyl)-butene, 2-methyl-1-(p-tolyl)-butane or a mixture thereof to cyclization and dehydrogenation in the presence of a catalyst comprising lead oxide and/or indium oxide and aluminum oxide. However, similar to the known methods described before, this method intends to make DMN's which belong to the same CMN triad as 2,6-DMN.

As regards the second method stated above for making DMN's, several patents (e.g., U.S. Pat. No. 4,963,248; Japanese Patent Nos. 02,247,136, 02,247,137, 02,304,034 and 03,038,532) describe the reforming of hydrotreated kerosene fractions and recovery of DMN's from the reformate. These references claim improved results are obtained by first removing the normal paraffins from the kerosene fraction using molecular sieve separations. Reforming is typically done over a platinum on alumina catalyst at 750–1020° F. and about 350 psig in the presence of hydrogen to obtain a reformate containing about 18 percent DMN's. 2,6-DMN can be separated from the reformate via distillation, molecular sieve adsorption, crystallization or complexation. This method does not meet the current requirements for economy since the process results in a low DMN yield and even lower 2,6-DMN yield. In addition, the resulting DMN mixture usually consists of all 10 DMN isomers, which is typical of the DMN products directly manufactured from refinery streams and results in inefficiency in the subsequent steps of producing 2,6-DMN via isomerization and separations.

As regards the third method stated above for making DMN's, several references teach recovery of 2,6-DMN from FCC Light Cycle Oil (proposed in a study by Eldib Engineering Co., see *Chemical Week*, Jun. 24, 1992, p. 27; *European Chemical News*, Sep. 28, 1992, p. 30; *Chemical Marketing Reporter*, Oct. 12, 1992; *Chemical Week*, Nov.

14, 1992, p. 39). As disclosed, the material, which is ordinarily used as a diesel fuel blendstock, contains about 1.75% 2,6-DMN. It is disadvantageously accompanied by all other 9 DMN isomers as in the case of kerosene described above. A key problem with this approach is that the FCC Cycle Oil contains high concentrations of sulfur and nitrogen compounds. These contaminants poison zeolites used in recovery of 2,6-DMN and also isomerization catalysts. To remove the sulfur and nitrogen compounds and to reduce them to about 10 ppm each, hydrotreating at severe conditions is required. Hydrotreating under such severe conditions inevitably causes hydrogenation and hydrocracking of DMN's, resulting in a great reduction in the yield of DMN's.

As regards the fourth method stated above for making DMN's, several patents teach methods of manufacturing DMN's by transalkylation of naphthalene or 2-methyinaphthalene. These patents are, for example, U.K. Patent No. 2,246,788A and European Patent No. 0,494,315 A1. However, it is apparent that such methods are always associated with by-products such as tricilkylnaphthalenes and have a low efficiency. These by-products are undesirable due to reduced yield of the desired products and added complexity and cost to the process because of the need for further separation steps. Similar drawbacks are also unavoidable with the methods of making DMN's by alkylation of naphthalene or methyinaphthalenes.

Accordingly, there exists a need in the petroleum industry for a lower-cost method than presently exists of producing DMN's. The method of this invention provides such a method.

SUMMARY OF THE INVENTION

The method of the invention utilizes amorphous catalysts in the reforming step which are superior in performance to those catalysts previously taught for use in making DMN's. Due to the recent efforts to increase oxygenate content of fuels, tertiary-amyl-methyl ether ("TAME") units are in operation in many petroleum refineries. The raffinate streams of TAME units contain $C_5$ olefins. In addition, an FCC $C_5$ stream also comprises $C_5$ olefins. In some embodiments of the invention, this raffinate and/or FCC $C_5$ stream are advantageously as a relatively low-cost feed stream for the production of pentyltoluenes, which then are used in making DMN's. The invention in some embodiments includes the discovery of performance enhancing properties of having a co-feed/diluent in the reforming step.

In one embodiment, the invention includes a method of making DMN's, including contacting in a reforming zone a pentyltoluenes containing feed with a platinum-containing amorphous reforming catalyst, containing a metal selected from the group consisting of a non-platinum Group VIIIB metal, rhenium, germanium, tin, lead, gallium, indium, and mixtures thereof, at reforming conditions, where at least a portion of the pentyltoluenes is converted to DMN's.

In another embodiment, the invention includes a method of making DMN's, the method including passing a $C_6$–$C_{12}$ naphtha-containing stream and a pentyltoluenes-containing stream to a reforming zone containing an amorphous platinum/alumina reforming catalyst; contacting in the reforming zone, the $C_6$–$C_{12}$ naphtha-containing stream and the pentyltoluenes and the reforming catalyst, under reforming conditions, where: at least a portion of the pentyltoluenes is converted to DMN's; and at least a portion of the $C_6$–$C_{12}$ naphtha is converted to aromatics.

In another embodiment, the invention includes a method of making DMN's, the method including passing a diluent stream, selected from benzene, toluene, xylenes, or $C_5$ naphtha, and a pentyltoluenes-containing stream to a reforming zone containing an amorphous platinum/alumina reforming catalyst; contacting in the reforming zone, the diluent stream and the pentyltoluenes and the reforming catalyst, under reforming conditions, where at least a portion of the pentyltoluenes is converted to DMN's.

In yet another embodiment, the invention includes a method of making DMN's, the method including: contacting in an alkylation zone, at a temperature of from about 32° F. to about 500° F. and a pressure of from about ambient to about 500 psig, a toluene-containing stream with a pentene-containing TAME raffinate stream in the presence of an acid alkylation catalyst selected from the group consisting of aluminum chloride, acid clays, heteropolyacids, acidic zeolites having a pore diameter of at least about 4.5 angstroms, solid-phosphoric acid catalysts, and mixtures thereof, where at least a portion of the toluene and pentene-containing TAME raffinate react to form pentyltoluenes; recovering from the alkylation zone at least a portion of the pentyltoluenes; passing a $C_7$ naphtha-containing stream and at least a portion of the pentyltoluenes to a reforming zone containing an amorphous platinum/alumina reforming catalyst including a metal selected from the group consisting of a non-platinum Group VIIIB metal, rhenium, germanium, tin, lead, gallium, indium, and mixtures thereof; contacting in the reforming zone, the $C_7$ naphtha-containing stream and the pentyltoluenes and the reforming catalyst, under reforming conditions including a pressure from about ambient to about 500 psig and a temperature from about 700° F. to about 1000° F., where: at least a portion of the pentyltoluenes is converted to DMN's; and at least a portion of the $C_7$ naphtha is converted to toluene; and recovering from the reforming zone at least a portion of the DMN's; passing at least a portion of the toluene produced in the reforming zone to the alkylation zone.

DETAILED DESCRIPTION OF PREFERRED EMBODIMENTS

A. Steps of the Process

Figure 1:
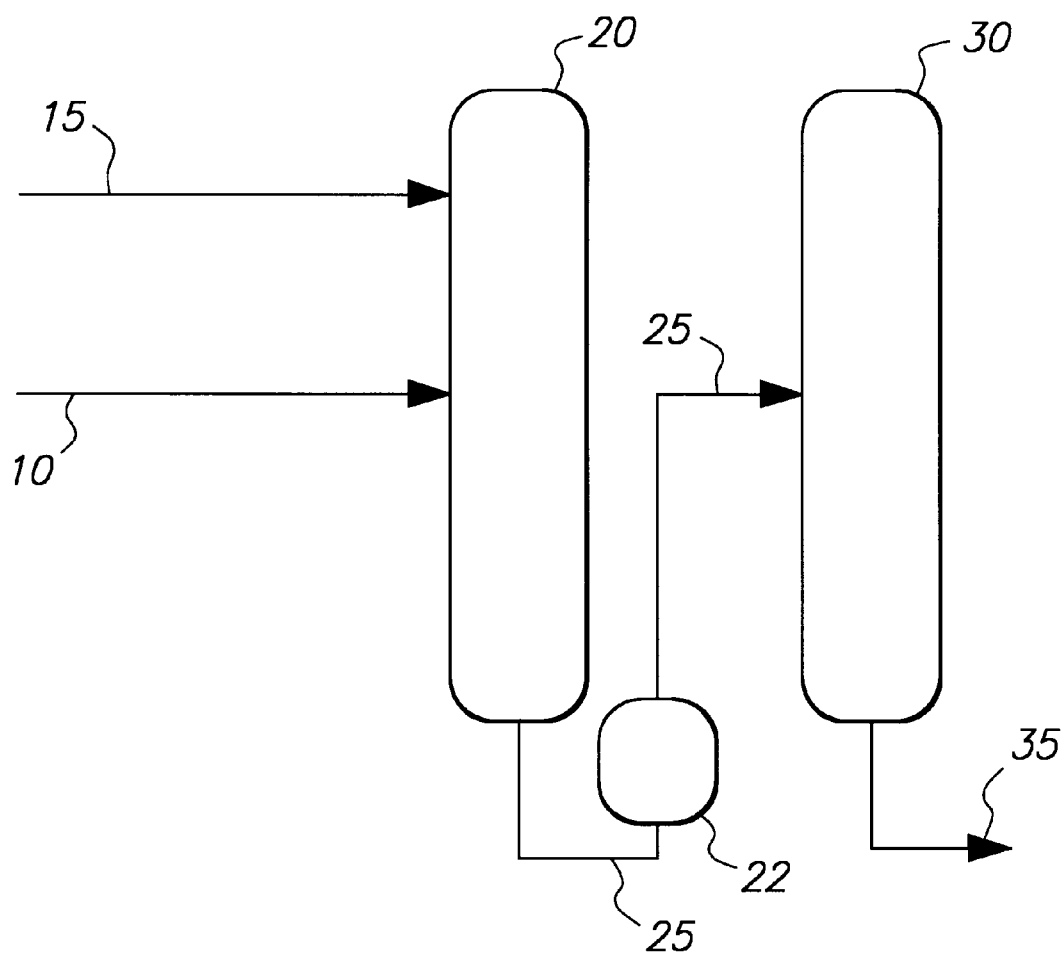
FIG. 1 depicts, in one embodiment, a simplified schematic process flow diagram of the method of the invention.

In one embodiment, the method of the invention includes contacting an alkylated toluene with a reforming catalyst, at reforming conditions, wherein at least a portion of the alkylated toluene is converted to DMN's. The alkylated toluene is all kylated with an alkyl group which includes, but is not limited to, a pentyl or pentenyl group.

In another embodiment, the alkylated toluene is the product of contacting, in an alkylation unit, at alkylation conditions, in the presence of an alkylation catalyst, toluene with a pentene-containing stream. The pentene-containing stream is optionally a TAME unit raffinate, a mixture of pentenes obtained from selective dehydrogenation of pentanes, purchased 1-pentene, an FCC $C_5$ stream (with or without having any iso-amylene removed), a $C_5$ olefin containing stream from an elhylene or naphtha cracker, a resid coking unit, an olefin metathesis unit, an olefin oligomerization unit producing $C_5$ olefins as a side product, a $C_5$ olefin-containing stream from alcohol dehydration. The olefin streams, or both the olefin and aromatic streams, are optionally fed by staged addition.

When the pentene-containing stream is from a TAME raffinate, the TAME raffinate stream is any conventional TAME raffinate stream containing pentenes. Optionally, a separate conventional adsorbent step may be used for removal of iso-amylene. The conversion of pentyltoluenes to pentenyltoluene is a process option discussed later in this description.

The toluene-containing stream is optionally pure, i.e., not obtained from a refinery stream, although various concentrations are possible. Alternatively, the toluene-containing stream is obtained from any conventional refinery stream containing toluene. These two streams are both fed to an alkylation zone. The streams are optionally mixed either prior to or after entering the alkylation zone. The alkylation zone utilizes any conventional alkylation process. The units in the alkylation process will typically include a reactor and one or more distillation columns for fractionating the alkylation reactor product. In another embodiment of the invention, the pentyltoluenes are prepared via alkylation steps other than toluene alkylation with $C_5$ olefins. For example, pentyltoluenes and/or pentenyltoluenes are optionally prepared via base-catalyzed alkylation of xylene(s) with $C_4$ olefins and/or $C_4$ dienes.

In the embodiment utilizing toluene and a $C_5$ olefin containing stream, at least a portion of the pentenes and toluene are converted in the alkylation unit to pententyltoluenes. Such process should include an acid alkylation catalyst. Such catalyst is optionally selected from the group consisting of aluminum chloride, acid clays, solid phosphoric acid catalysts, heteropolyacids, acidic zeolites having a pore diameter of at least about 4.5 angstroms, and mixtures thereof. Acidic zeolites having a pore diameter of at least about 4.5 angstroms include, but are not limited to, the following zeolites: Y zeolite, beta zeolite, mordenite, offretite, omega, ferrierite, SSZ-20, SSZ-24, SSZ-25, SSZ-26, SSZ-31, SSZ-32, SSZ-33, SSZ-35, SSZ-37, SSZ-42, SSZ-44, EU-1, NU-86, NU-87, UTD-1, ZSM-5, ZSM-11, ZSM-12, ZSM-35, ZSM-48, MCM-22, MCM-36, MCM-56, and mixtures thereof. In one embodiment, the acid alkylation catalyst is preferably a Y-zeolite type catalyst. The alkylation catalyst optionally includes up to 80 weight percent alumina as binder, preferably up to 50 weight percent alumina.

To prevent the formation of tri-substituted benzene compounds during the alkylation of toluene to pentyltoluenes, it is favorable to have toluene in stoichiometric abundance. Unreacted toluene is generally separated from the pentyltoluenes before the pentyltoluenes are dehydrocyclized. Based on the results demonstrated in Example 19 below, the separation of toluene from pentyltoluenes after the alkylation step may not be required before the reforming step of pentyltoluenes to DMN's.

In addition, the separation of the $C_5$ alkanes/naphthenes, which are inert for toluene alkylation and may be present in the $C_5$ olefin stream, from $C_5$ olefins before or after toluene/$C_5$ olefin alkylation step may not be required. These $C_5$ alkanes/naphthenes may be used as diluent for the reforming of pentyltoluenes to DMN's as well. One or more conventional separation units may be used to separate out unreacted pentenes and toluene. Optionally, distillation units are utilized to further purify the pentyltoluenes. Optionally, some or all of any dipentyltoluenes by-product formed in the alkylation zone is removed from the alkylation zone product. At least a portion of the pentyltoluenes stream recovered from the alkylation zone, and optionally any unseparated dipentyltoluenes, are then passed to a reforming zone to make DMN's. It is optionally passed as-is or with a diluent or a co-feed. The diluent is an inert-acting solvent, e.g., excess toluene, benzene, xylenes, $C_5$ naphtha, or mixtures thereof. Suitable co-feeds are $C_6$–$C_{12}$ naphthas. These co-feeds optionally serve both as diluents and as reactants. They typically reform to aromatics. Where $C_7$ naphtha is used as a co-feed, a portion of the $C_7$ naphtha is typically converted to toluene in the reforming zone. That toluene is then optionally separated from the other reformer effluents for recycle to the alkylation unit to make pentyltoluenes. In the reformer unit, the weight ratio of co-feed or diluent to pentyltoluenes containing feed is from about 0:1 to about 1000:1, preferably from about 1:1 to about 100:1.

That reforming zone utilizes any conventional reforming reactor bed arrangement. The reforming zone contains a reforming catalyst, e.g., a dehydroaromatizing catalyst. This catalyst is preferably one with high DMN selectivity and low hydrocracking selectivity. Suitable catalysts are platinum-containing amorphous reforming catalysts which optionally contain a metal selected from the group consisting of a non-platinum Group VIIIB metal, rhenium, germanium, tin, lead, gallium, indium, and mixtures thereof. Any conventional impregnation, mulling, ion exchange or other known methods for adding the metals may be used. The support of the amorphous catalysts is optionally selected from the group consisting of alumina, silica, titania, vanadia, chromia, zirconia, and mixtures thereof. Preparations of such catalysts are taught, e.g., in U.S. Pat. Nos. 3,415,737; 4,636,298; and 4,645,586, the disclosures of which are incorporated herein by references. In one preferred embodiment, the reforming catalyst is preferably a non-zeolitic platinum-rhenium catalyst supported on alumina. Commercial examples of such catalysts are, for example, (1) AR405, CR 201/301/401, E1000, E301, E302, E603, E611, E802, E803, RG492 and RG582 from ACREON CATALYSTS/PROCATALYSE; (2) CK-300's, CK-433, CK-522 Trilobe, KC-542 Trilobe, ARC-555, ARC-111E and ARC-111B from AKZO NOBEL; (3) PHF-5, PRHF-30/33/37/50/58, KX-120/130/160, PHF-4, P-8, PR-8, PR-9, PR-28, PR-29, IMP-RNA-2/4, PS-7, PS-10, PS-20, PS-30 and PS-40 from CRITERION CATALYST CO. LP; (4) R-30, R-32, R-34, R-50, R-51, R-56, R-60, R-62, R-132, R-134 and R-72 from UOP (see the "*OGJ Special Worldwide Catalyst Report*" in *Oil & Gas Journal*, Oct. 6, 1997, p. 43); and (5) Rhen-F and Rhen-H from Chevron.

In the reforming stage, the pentyl group is dehydrogenated and cyclized intramolecularly to produce DMN's. Preferably, the formation of ethylnaphthalenes ("EN") is low or negligible. This is because their boiling points are very close to those of DMN's and, therefore, they are difficult to separate out. Optionally, one or more separation units are used to recover the DMN's, especially 2,6-DMN. As a result of the reforming, at least a portion of the pentyltoluenes is converted to DMN's. The preferable form is 2,6-DMN. The effluent from the reforming zone is passed to a separation zone for recovery of at least a portion of the DMN product. Any conventional separation methods are optionally utilized. Optionally, the DMN's are further purified and isomerized to increase yield of 2,6-DMN. Where only partial conversion of pentyltoluenes to DMN's is achieved, the process optionally includes a separation stage for recovering at least a portion of the pentyltoluenes not converted to DMN's. At least a portion of any unconverted pentyltoluenes is then, optionally, recycled to the reforming unit.

The reformer unit utilized in the present invention is optionally either a dedicated unit or a multipurpose unit. That is, in one embodiment, the reformer unit is dedicated to the production of DMN's. In another embodiment, the reformer unit has feed streams other than for the production of DMN's and makes products other than DMN's. For example, reformers are also utilized in the production of gasoline range aromatics and for making benzene. This latter embodiment is economically beneficial since there are no capital costs of constructing a dedicated reformer unit. That is, a relatively small stream of pentyltoluenes is co-fed into the naphtha feed stream of an existing reformer. Naturally, a separation step follows the reformer to separate the DMN's from any other reformer products. Steps of treating the reformer effluent for increasing the yield of and/or purifying the preferred 2,6-DMN optionally follow the reformer unit. One such optional step is isomerization of the reformer effluent to increase the yield of 2,6-DMN. Santilli and Chen, U.S. patent application Ser. No. 08/892,508 ("the '508 Application"), which is incorporated herein by reference, discloses a method of isomerizing a feed of any composition of mixed DMN's having a methyl group on each ring to a product that approximates an equilibrium mixture of mixed DMN's having a methyl group on each ring (i.e., the 2,6-DMN and 2,7-DMN triads). A method utilizing crystallization and adsorption for purifying the 2,6-DMN from the reformer effluent is taught by Munson, Bigot, and He, U.S. patent application Ser. No. 09/000,858, which is incorporated herein by reference. One or more embodiments of the method of the present invention optionally incorporate these methods, separately and/or in combination. These methods of purification and isomerization enhance the value of the present invention for making a mixture of DMN's which belong to the 2,6-DMN and 2,7-DMN triads. That is, where 2,6-DMN is the desired end product, being able to produce a mixture of DMN's is valuable in itself where methods exist for then isomerizing/purifying that mixture into 2,6-DMN. This provides an economic benefit where the feed streams for producing a mixture of DMN's through alkylation and reforming are less expensive than the feed streams necessary for producing mainly 2,6-DMN through alkylation and reforming.

The isomerization method taught in the '508 Application solves a long felt need to overcome a fundamental complication in the commercial production of 2,6-DMN. That fundamental complication is the difficulty of converting DMN isomers other than 2,6-triad DMN's into the desired 2,6-DMN isomer. There are ten different isomers of DMN's. Of these, nine of them can be grouped into three triads based on the relative ease of acid-catalyzed isomerization within a certain triad. Such an intra-triad isomerization can be done using a wide variety of solid acids as catalysts. This ease of acid-catalyzed isomerization within a triad is based on the fact that a methyl group on naphthalene shifts relatively easily from an alpha position to a beta position or vice versa on the same ring but does not shift easily from a beta position to another beta position on the same ring or from an alpha position to another alpha position. The three triad groups are as follows: 2,7-DMN, 1,7-DMN and 1,8-DMN; 2,6-DMN, 1,6-DMN and 1,5-DMN; and 1,4-DMN, 1,3-DMN and 2,3-DMN. The tenth isomer, 1,2-DMN, consists of two methyl groups in adjacent alpha and beta positions and does not fall into one of the aforementioned triads.

In conventional methods, DMN manufacturers have focused on developing the methods (vide supra) for making commercial quantities of 2,6-DMN by avoiding co-producing other DMN isomers because of the difficulty in recovering 2,6-DMN at high yield in the presence of other DMN isomers. Based on the above described DMN triad chemistry, DMN manufacturers have tried to avoid making isomers outside the 2,6-triad because of the difficulty in isomerizing across triads and the associated unavoidable side-reactions such as cracking, dealkylation and transalkylation. Isomers that cannot be converted to 2,6-DMN represent a yield loss and inefficient use of raw materials. Adsorption separation and purification of the 2,6-DMN are not practical when the concentration of 2,6-DMN in the feed stream is low. This is because there are no known materials that will preferentially adsorb 2,6-DMN over the other isomers. These limitations often necessitate the use of expensive raw materials and controlled organic synthesis reactions that can produce only isomers in the 2,6-triad, such as alkylation of butadiene and ortho-xylene.

Thus, previous isomerization technologies have been limited to intra-triad conversions, where the technologies of manufacturing 2,6-DMN are, therefore, preferably those which mainly make 2,6-triad DMN's. Briefly, the new method taught in the '508 Application consists of hydroisomerization of DMN's over a bifunctional catalyst (metal and acid) and subsequent dehydrogenation of the resulting partially and/or fully saturated DMN's. Thus, this new method opens up a new opportunity of more efficiently making 2,6-DMN from not only 2,6-triad but also 2,7-triad. Again, this new isomerization enhances the value of the instant method since it lifts the limitation on making 2,6-DMN from the precursors which mainly make 2,6-triad DMN isomers.

B. Process Conditions

The alkylation zone, reforming zone, and any separation zones are each operated under conventional operating conditions, e.g., pressure, temperature, and flow rates. Such conditions are known in the art. Typical alkylation conditions, e.g., include a temperature from about 32° F. to about 500° F., a pressure from about ambient to about 500 psig, preferably from about ambient to about 300 psig for a Y-zeolite, and preferably from about 32° F. to about 300° F. for $AlCl_3$ and from about 100° F. to about 400° F. for a Y-zeolite. In one embodiment, a preferred toluene to pentenes molar ratio is from about 4:1 to about 12:1 and the Weight Hourly Space Velocity ("WHSV") of the feed is from about 1 $h^{-1}$ to about 8 $h^1$.

Conventional residence times are used as appropriate for each particular catalyst. An acid zeolitic alkylation catalyst such as Y-zeolite is preferred since it can be regenerated and reused. In contrast, $AlCl_3$ cannot be reused. Typical alkylation zone conditions and catalysts are taught, e.g., in U.S. Pat. No. 5,149,894, the disclosure of which is incorporated herein by reference.

Typical reforming conditions, e.g., are a temperature from about 700° F. to about 1000° F., a pressure from about ambient to about 500 psig. In one preferred embodiment, the pressure is from about ambient to about 300 psig, the temperature is from about 800° F. to about 1000° F., and the catalyst is a Pt—Re/Al$_2$O$_3$/Cl amorphous reforming catalyst. The Weight Hourly Space Velocity (WHSV) of pentyltoluenes is typically from about 0.01 to about 100 h$^{-1}$, in some embodiments preferably from about 0.1 h$^{-1}$ to about 10 h$^{-1}$, more preferably from about 0.1 h$^{-1}$ to about 1h$^{-1}$. The molar ratio of hydrogen to hydrocarbon feed is typically from about 1:1 to about 15:1. In some embodiments, the ratio is preferably from about 1:1 to about 6:1. Conventional residence times are used as appropriate for each particular catalyst. Typical reforming conditions are taught, e.g., in U.S. Pat. Nos. 5,401,386, 5,328,595, and 4,645,586, the disclosures of which are incorporated herein by references.

Optionally, prior to passing the pentyltoluenes to the reforming zone, at least a portion of the pentyltoluenes is converted to pentenyltoluenes. This is accomplished by contacting at least a portion of the pentyltoluenes with a conventional dehydrogenation catalyst at conventional dehydrogenation conditions. As a result, at least a portion of the pentyltoluenes is dehydrogenated to form pentenyltoluenes.

Thus, a mixture of pentyltoluenes and pentenyltoluenes is formed. Preferably, the mixture contains from about 10 weight percent to about 90 weight percent pentenyltoluenes. More preferably, the mixture contains from about 25 weight percent to about 65 weight percent pentenyltoluenes. At least a portion of this mixture is passed to the reforming zone for contact with the reforming catalyst as described above. Optionally, pentenyltoluenes are produced via toluene alkenylation with pentadienes on acid catalysts. The production of pentenyltoluenes via toluene alkenylation with pentadienes is optionally accomplished together with the production of pentyltoluenes via toluene alkylation with pentenes in the same process step.

DETAILED DESCRIPTION OF THE DRAWINGS

Modifications of the process that is shown in the drawings and described in this specification that are obvious to those of ordinary skill in the oil refinery process art are intended to be within the scope of the invention.

Figure 2A:
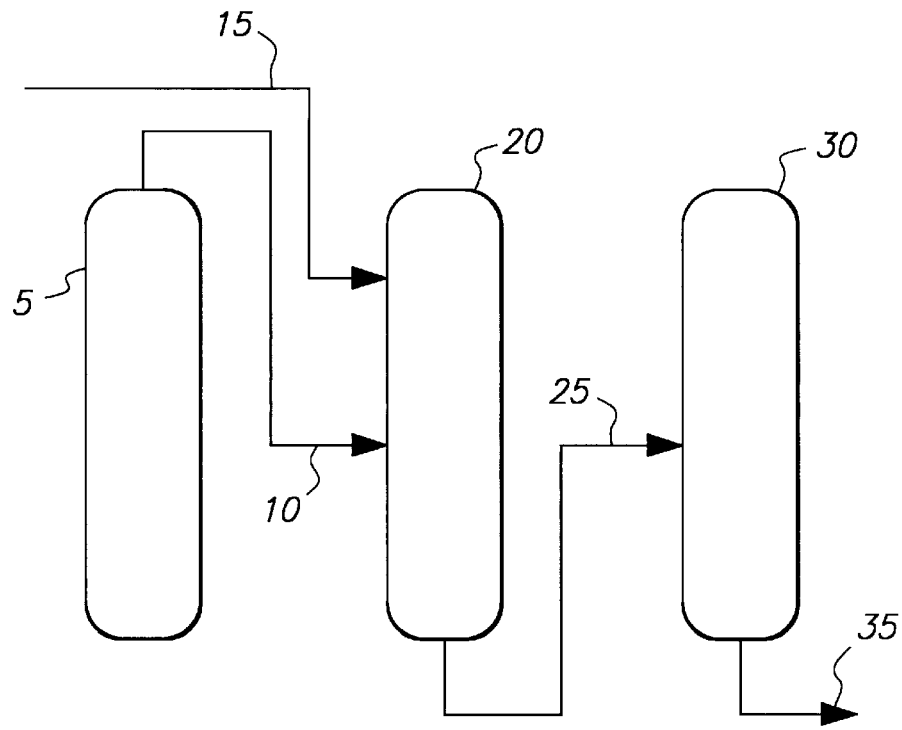
FIG. 2A is the same as FIG. 1, except that it does not show a dehydrogenation unit between the alkylation zone and reforming zone and does show a TAME unit as the source of the pentene-containing feed stream.
Figure 2B:
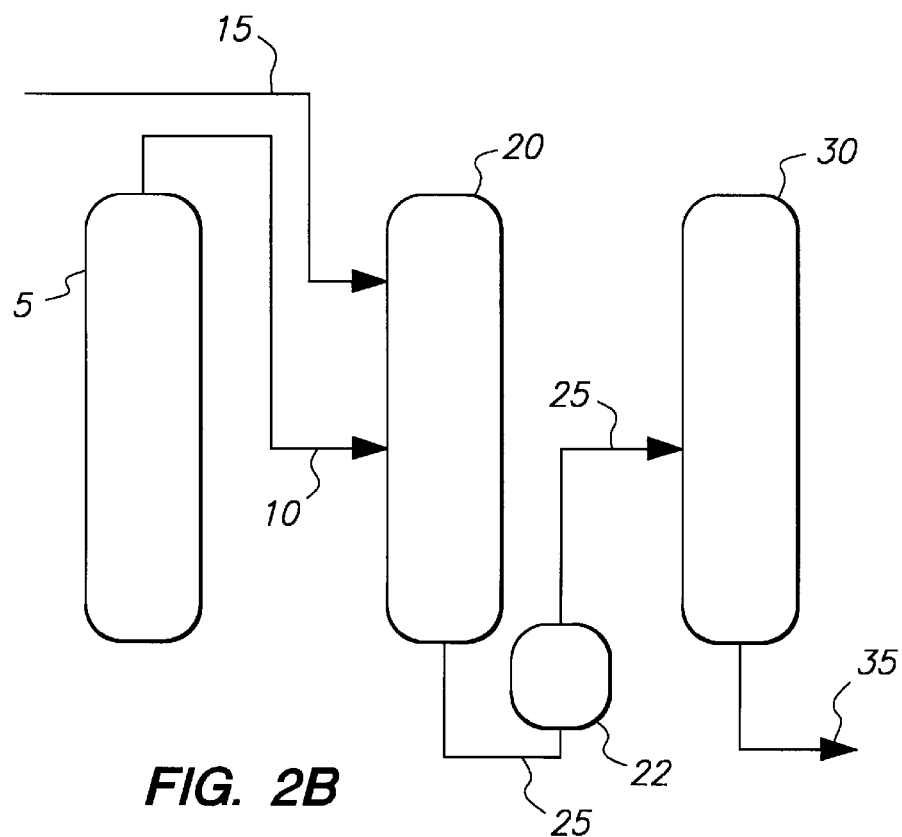
FIG. 2B is the same as FIG. 2A, except that it shows a dehydrogenation unit between the alkylation zone and reforming zone.

One embodiment of the process of the invention is illustrated in the FIG. 2B. A toluene-containing stream 15 is contacted with a pentene-containing TAME raffinate stream 10 obtained from TAME unit 5. The contacting occurs in alkylation zone 20 in the presence of an acid alkylation catalyst (not shown). At least a portion of the toluene and pentenes react to form pentyltoluenes. Pentyltoluenes are recovered in stream 25.

At least a portion of pentyltoluenes stream 25 is passed to a reforming zone 30. The reforming zone 30 contains a dehydroaromatizing type catalyst (not shown). In reforming zone 30, the pentyltoluenes in stream 25 are contacted with a dehydroaromatizing type catalyst (not shown) under reforming conditions. At least a portion of the pentyltoluenes is converted to DMN's, preferably 2,6-DMN. At least a portion of the DMN's is recovered as stream 35.

Optionally, prior to passing stream 25 to the reforming zone 30, it is first passed to optional dehydrogenation unit 22. In dehydrogenation unit 22, pentyltoluenes are contacted with a conventional dehydrogenation catalyst at conventional dehydrogenation conditions. As a result, at least a portion of the pentyltoluenes is dehydrogenated to form pentenyltoluenes.

FIG. 2A is the same as FIG. 2B, except that it does not show a dehydrogenation unit 22 between the alkylation zone 20 and reforming zone 30. FIG. 1 is the same as FIG. 2B, except that it does not show TAME unit 5 and stream 10 is any C$_5$ olefin containing stream.

Figure 3:
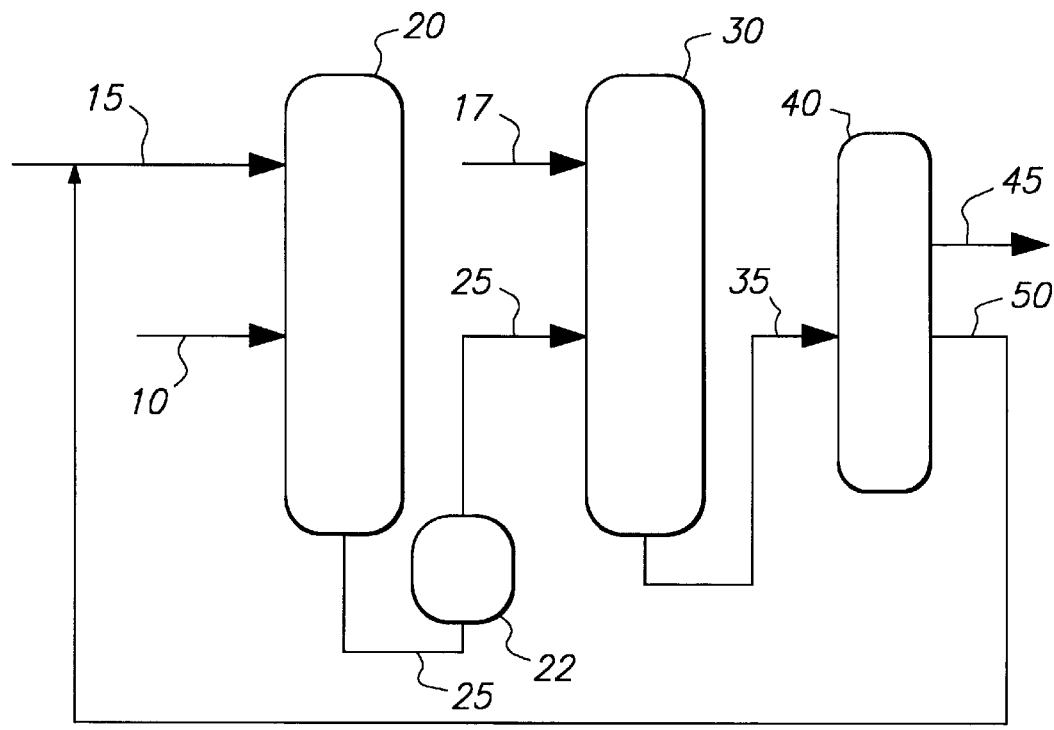
FIG. 3 is the same as FIG. 1, except that it shows a separation zone following the reforming zone, shows a co-feed/diluent stream to the reforming zone, and shows a recycle stream from the separation zone to the alkylation zone.

FIG. 3 is the same as FIG. 1, except that it shows a separation zone 40 following the reforming zone 30, shows a co-feed/diluent stream 17 to the reforming zone 30, and shows a recycle stream 50 (e.g., for recycle of toluene produced from reforming a C$_7$ naphtha co-feed) from the separation zone 40 to the alkylation zone 20. At least a portion of the DMN's is recovered as stream 45.

Figure 4:
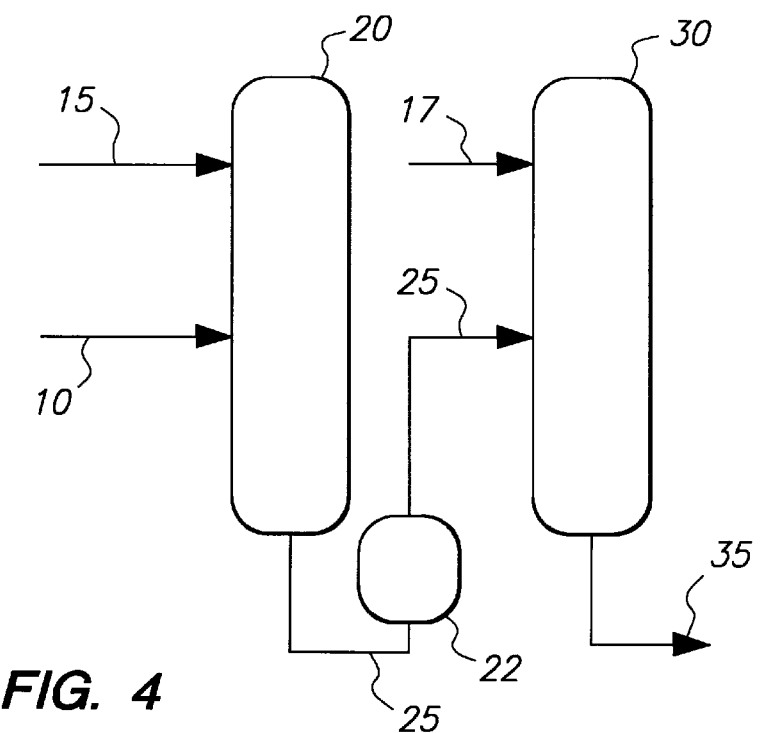
FIG. 4 is the same as FIG. 1, except that it shows a co-feed/diluent stream to the reforming zone.

FIG. 4 is the same as FIG. 1, except that it shows a co-feed/diluent stream 17 to the reforming zone 30.

ILLUSTRATIVE EMBODIMENTS

EXAMPLE 1

Toluene Alkylation with TAME Raffinate and 2-Pentene over Zeolite Y

A catalyst was made by binding 80% Y zeolite and 20% alumina, extruding, and calcining at 1100° F. This catalyst was crushed and sieved to give particles in the 20/40 mesh size range. A 1.0 gram sample of the sized Y zeolite catalyst was packing in a ½" OD tubular reactor such that the catalyst was located in the isothermal region of a single zone electrically heated furnace containing the reactor. Packing of inert alundum was placed above and below the catalyst to hold it in place. A flow of dry nitrogen gas at 100 sccm was introduced and the catalyst heated to 392° F. The catalyst was maintained at 392° F. for 12 hours and then cooled to room temperature. Toluene was then introduced into the reactor in the upflow mode at ca. 0.25 ml/minute. After about one hour, the pressure was increased to 175 psig by means of a back pressure regulator. After the pressure stabilized, the reactor was heated to 320° F. When the temperature stabilized, the toluene flow was stopped and was replaced with a feed containing toluene and TAME raffinate at a flow rate of 2.48 ml/hour. TAME raffinate is a stream consisting mainly of C$_5$ species (containing about 35% pentenes) from the effluent of a reactor making TAME (tertiary amyl methyl ether).

The feed composition was such that the toluene/pentenes molar ratio was equal to 10:1. Samples of the reactor effluent were periodically collected and analyzed by gas chromatography. Results are shown in Table 1 below. During much of the run, olefin conversion was essentially 100% (i.e., >99 mole %). At 287.5 hours into the run, the feed rate was increased to give a WHSV of 3.2 h$^{-1}$. Olefin conversion decreased slightly. With a further increase of WHSV to 4.2 h$^{-1}$ at 305 run hours, olefin conversion decreased slightly again but still remained above 98 mole %. At 336 hours, the feed was changed to a feed based on 2-pentene (i.e., a simulated feed containing 2-pentene, n-pentane, and toluene of the same approximate composition as the TAME raffinate feed) and the WHSV increased to 6.0 h$^{-1}$, causing a decrease in olefin conversion to 88.5 mole %. With a decrease in WHSV to 2.0 h$^{-1}$ at 59 hours, some of the conversion loss was restored and with a further decrease in WHSV to 1.0 h$^{-1}$ at 380 hours, olefin conversion increased to 98.5 mole %. The run was finally ended at ca. 480 hours. This example shows the robustness and long catalyst life of a Y zeolite catalyst for the alkylation of toluene with pentenes.

TABLE 1

Selected Yields and Selectivities of Toluene Alkylation with Pentenes at 320° F.
(Selectivities Calculated on Mole % Olefin Consumed Basis)

| Sample Number | Run Hours | WHSV, $h^{-1}$ | Pentene Source | Olefin Conv. Mole % | Pentyl-toluene Yield, Mole % | Dipentyl-toluene Yield, Mole % | Heavies[a] Yield, Mole % |
|---|---|---|---|---|---|---|---|
| 13 | 160.5 | 2.1 | TAME Raffinate | 99.9 | 83.5 | — | — |
| 14 | 173 | 2.1 | TAME Raffinate | 99.9 | 75.1 | 6.7 | 4.1 |
| 18 | 280 | 2.1 | TAME Raffinate | 99.4 | 84.7 | 3.7 | 2.1 |
| 23 | 300 | 3.2 | TAME Raffinate | 98.7 | 85.9 | 3.0 | 2.7 |
| 24 | 324 | 4.2 | TAME Raffinate | 98.6 | 90.0 | 1.6 | 0.5 |
| 25 | 852 | 6.0 | 2-pentene | 88.5 | 88.4 | 11.1 | 0.2 |
| 26 | 373 | 2.0 | 2-pentene | 89.7 | 90.2 | 9.4 | 0.2 |
| 27 | 469 | 1.0 | 2-pentene | 98.5 | 92.6 | 6.8 | 0.5 |

[a]Calculated as pentene oligomer.

EXAMPLE 2

Toluene Alkylation with TAME Raffinate over Various Zeolites

Other zeolitic catalysts were tested for the alkylation of toluene with pentenes. The procedure for the alkylation runs was the same as described in Example 1. Catalyst descriptions and experimental conditions for these runs are listed in Table 2.

EXAMPLE 4

Toluene Alkylation with TAME Raffinate over Zeolite Y 6.5 grams of zeolite Y were dehydrated in $N_2$ flow at 572° F. for 1 hour. 368 grams of toluene and 80 grams of TAME Raffinate (containing about 5% pentenes) were mixed with the zeolite Y dehydrated above. The mixture was heated at 302–311° F. under autogenous pressure in a stirred autoclave

TABLE 2

Results of Alkylation Experiments with Pentenes over Zeolitic Catalysts

| Run | Catalyst | Form | Catalyst Wt, g | Pentene source | WHSV $h^{-1}$ | Pressure, psig | Activation temp, ° F. | Alkylation temp, ° F. | Run length, hours | Olefin Conv, % |
|---|---|---|---|---|---|---|---|---|---|---|
| 2A | Beta zeolite | bound extrudate, crushed to 20/40 mesh | 1.6 | TAME Raffinate | 2 | 175 | 392 | 320 | 160 | ~100 |
| 2B | SSZ-25 | pelletized powder, 20/40 mesh | 1.7 | TAME Raffinate | 2 | 175 | 392 | 338 | 209 | ~100 |
| 2C | Al-SSZ-33 | pelletized powder, 20/40 mesh | 1.5 | TAME Raffinate | 2, 4[a] | 175 | 392 | 320 | 186 | ~100, ~75[b] |

[a]WHSV increased to 4 at 40 run hours.
[b]Conversion at 4 $h^{-1}$ WHSV.

EXAMPLE 3

Toluene ALkylation with 1-Pentene over Zeolite $AlCl_3$ 3220 grams of toluene and 4 grams $AlCl_3$ were added into a 5 liter flask cooled to <10° C. by using an ice bath. Then slowly add 490 grams of 1-pentene under stirring over 2 hours. Subsequently stir the mixture overnight. After the reaction, 350 ml of water were then added. The aqueous layer was separated and discarded. The organic layer was washed with additional water and dried with $MgSO_4$. This reaction produced a hydrocarbon mixture containing pentyltoluenes. The dried solution was concentrated by removing most of the extra toluene by distillation. The resulting distillate was analyzed by gas chromatography. About 1100 grams of pentyltoluenes were obtained.

for 4.5 hours. The mixture was then cooled to ambient temperature and filtered. The pentyltoluenes were collected from the reaction products by distillation. The resulting distillate was analyzed by gas chromatography. About 49 grams of pentyltoluenes were obtained.

EXAMPLE 5

Toluene Alkylation with TAME Raffinate over $AlCl_3$ 920 grams of toluene were mixed with 0.65 grams of anhydrous $AlCl_3$ as catalyst. To this mixture, 70 grams of TAME raffinate (containing about 35% pentenes) were added dropwise over a six-hour period. The solution was stirred magnetically at room temperature overnight.

Subsequently, 0.66 grams of anhydrous AlCl$_3$ were added to the mixture. The temperature was raised to 140° F. for four hours. 100 ml of water were then added. The aqueous layer was separated and discarded. The organic layer was washed with additional water and dried with MgSO$_4$. This reaction produced a hydrocarbon mixture containing pentyltoluenes. The dried solution was concentrated by removing most of the extra toluene by distillation. The resulting distillate was analyzed by gas chromatography. About 48 grams of pentyltoluenes were obtained.

EXAMPLE 6

Toluene Alkylation with FCC C$_5$'s over Zeolite Y

An FCC C$_5$ sample was taken from the refinery FCC unit and had the following approximate assay:

| | |
|---|---|
| 22.3% | isoamylene |
| 21.3% | n-pentenes |
| 0.03% | dienes |
| 1.4% | butenes |
| 1.5% | cyclopentene |
| 53.5% | others (paraffins, naphthenes) |

Toluene (2829 grams) and 463.3 grams of the above FCC C$_5$ sample were blended. In a 1 liter autoclave, 750 ml of the above toluene/FCC C$_5$ blend were combined with 13 grams of zeolite Y dehydrated in a N$_2$ flow at 595° F. for 3.5 hours. The resulting mixture was heated at 311° F. under autogenous pressure in a stirred autoclave for 1.75 hours. The mixture was then cooled to ambient temperature and filtered. The pentyltoluenes were collected from the reaction products by distillation. The resulting distillate was analyzed by gas chromatography. About 96 grams of pentyltoluenes were obtained.

EXAMPLE 7

Preparation of Reforming Catalysts

The representative non-zeolitic reforming catalyst tested for pentyltoluene reforming to DMN's was a Pt—Re/Al$_2$O$_3$/Cl catalyst comprising approximately 0.3 wt. % Pt, 0.6 wt. % Re and 1.0 wt. % Cl. Preparation procedures of these catalysts and their analogues with varying compositions are known to those skilled in the art.

EXAMPLE 8

Pretreatments of Reforming Catalysts

Depending on the properties of the catalysts used in the experiments of this invention, a pretreatment step called sulfiding may be required to reduce the hydrogenolysis activity. The sulfiding reaction of the Pt—Re/Al$_2$ O$_3$/Cl catalyst of Example 7 was conducted in down flow fixed bed reactor system. The procedure is described as follows:

The catalyst was meshed to 24–42 chips and then loaded into stainless steel tube reactors. The catalyst was first dried in a N$_2$ flow (300 ml/minute) from room temperature to 400° F. at a heating rate of 10° F./minute and kept at 400° F. for 30 minutes. The catalyst was then reduced as follows: the catalyst was heated in a H$_2$ flow (300 ml/minute) from 400° F. to 900° F. at a heating rate of 5° F./minute and keeping at 900° F. for 30 minutes. The catalyst was then cooled to 800° F. before starting the sulfiding reaction.

Sulfiding was accomplished by contacting a feed consisting of anhydrous n-octane containing 200 ppm sulfur (as dimethyl disulfide) with the catalyst using an H$_2$ carrier. The liquid feed flow rate was 0.43 ml/minute and the H$_2$ flow rate was 30 ml/minute. The sulfiding reaction was carried out at 800° F. and atmospheric pressure for 60 minutes.

After sulfiding, the catalyst was heated in a H$_2$ flow (300 ml/minute) from 800° F. to 900° F. within 10 minutes and then held at 900° F. for an additional 30 minutes in order to remove the excess sulfur species occluded in the pores and/or on the surface of the catalysts. Finally, the catalysts were cooled down to room temperature within 5 hours in the same H$_2$ flow (300 ml/minute).

EXAMPLE 9

Catalytic Testing Procedure for Reforming

Prior to the reforming testing, the catalysts (sulfided if required) were first dried in a N$_2$ flow (100 ml/minute) from room temperature to 400° F. at a heating rate of 10° F./minute and kept at 400° F. for 30 minutes. The catalysts were subsequently heated in a H$_2$ flow (100 ml/minute) from 400° F. to 900° F. at a heating rate of 5° F./minute and kept at 900° F. for 30 minutes. Finally, the catalysts were heated up or cooled down to the preset reforming temperature (e.g., 870° F. or 950° F.). At the same time, the reactor system was pressurized to the preset pressure (e.g., 50 or 130 psig) if pressures other than atmospheric pressure were required. Meanwhile, the H$_2$ flow was adjusted to the preset rate (e.g., 5 or 15 ml/minute).

The typical screening conditions for reforming were: 800–980° F., molar H$_2$:pentyltoluenes ratio of 1:1 to 15:1 and pentyltoluenes WHSV of 0.1 to 10 h$^{-1}$. The reaction pressure was varied in the range of ~5–300 psig. The feedstocks used were pentyltoluenes prepared over various catalysts such as AlCl$_3$ or zeolite Y via the toluene alkylation with various C$_5$ olefins such as 1-pentene, TAME raffinate or FCC C$_5$'s.

The reforming products and unconverted pentyltoluenes were analyzed using on-line GC (HP 5890 Series II equipped with a 50 meter long HP-1 or AT-35 capillary column), being capable of analyzing all resulting ethylnaphthalenes (EN) and dimethylnaphthalenes (DMN) except for the separation of 2,6-DMN and 2,7-DMN. The special design of the flow type reactor systems and the use of the high temperature resistant valves and tubings guaranteed the reliability of the on-line GC analysis. For the analysis of 2,6-DMN and 2,7-DMN, an off-line GC (HP 5880) which is coupled with a 120 meter long capillary column (a 60 meter long AT-35 capillary column connected with a 60 meter long AT-50 capillary column) was used. In addition, GC/MS was used also for product identification.

EXAMPLE 10

Pentyltoluene Reforming on Amorphous Catalyst versus L Zeolite Catalyst

This example compares the catalytic performance of a representative amorphous reforming catalyst to a zeolitic catalyst made from zeolite L (Pt/Ba/K-L). The pentyltoluene feed prepared in Example 3 from 1-pentene and toluene was reformed on the sulfided Pt—Re/Al$_2$ O$_3$/Cl catalyst from Example 7 and compared to an unsulfided Pt/Ba/K-L zeolite catalyst containing ~0.7 wt. % Pt, ~5 wt. % Ba, and ~1.0 wt. % K. The reaction conditions were as follows: 950° F., 50 psig and 200 psig, WHSV of 3 h$^{-1}$, and a molar H$_2$-topentyltoluenes ratio of about 5:1. The on-line GC analysis results collected at ~3 hours of reaction time are shown in Table 3. On the amorphous catalyst, the resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethyinaphthalenes (EN) was formed. The off-line GC analysis showed that the ratio of 2,6/2,7-DMN was about 1:1. With Pt/Ba/K-L zeolite catalyst, lower pentyltoluene conversion and lower DMN yield/selectivity were observed. Because of such low DMN yields over Pt/Ba/K-L zeolite catalyst, the selectivity of EN's and DMN's other than 1,5-DMN, 1,6-DMN, 1,7-DMN, 2,6-DMN and 2,7-DMN in the DMN products is higher than with the Pt/Al$_2$O$_3$/Cl catalysts. The results show that amorphous catalysts performed better for the formation of DMN's from pentyltoluenes.

TABLE 3

Reforming of Pentyltoluenes on Amorphous Catalyst versus Pt/Ba/K-L Zeolite Catalyst

| | Catalyst | | | |
|---|---|---|---|---|
| | Pt-Re/Al$_2$O$_3$/Cl | | Pt/Ba/K-L | |
| Temperature, °F. | 950 | 950 | 950 | 950 |
| Pressure, psig | 50 | 200 | 50 | 200 |
| WHSV, h$^{-1}$ | 3 | 3 | 3 | 3 |
| PT conversion, % | 100 | 100 | 55 | 95 |
| DMN yield, % | 66 | 27 | 8 | 4 |
| DMN selectivity, % | 66 | 27 | 14.9 | 4.2 |

EXAMPLE 11

Pentyltoluene Reforming on Pt—Re/Al$_2$O$_3$/Cl Catalyst at Various Temperatures and Pressures The pentyltoluene feed prepared in Example 3 from 1-pentene and toluene was reformed on the sulfided Pt—Re/Al$_2$O$_3$/Cl of Example 7 under various reaction conditions: 850–950° F., 50–130 psig, WHSV of 3 h$^{-1}$, and a molar H$_2$-to-pentyltoluenes ratio of about 5:1. The on-line GC analysis results collected at ~3 hours of reaction time are shown in Table 4. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. The results show that higher temperature and lower pressure were favorable for the formation of DMN's.

TABLE 4

Reforming of Pentyltoluenes on Pt-Re/Al$_2$O$_3$/Cl under Various Conditions (WHSV = 3 h$^{-1}$)

| | | | Yield, % | | | | |
|---|---|---|---|---|---|---|---|
| Condition | | PT Conv., | 1,5- | 1,6- | 1,7- | 2,6/2,7- | Total |
| T, °F. | P, psi | % | DMN | DMN | DMN | DMN | DMN's |
| 850 | 130 | 80 | 1.2 | 5.2 | 5.6 | 6.4 | 18.3 |
| 950 | 130 | 98 | 3.3 | 14.3 | 13.0 | 23.4 | 54.0 |
| 950 | 50 | ~100 | 6.1 | 19.3 | 18.5 | 22.1 | 66.0 |

EXAMPLE 12

Pentyltoluene Reforming on Pt—Re/Al$_2$O$_3$/Cl Catalyst at Various Weight Hourly Space Velocities The pentyltoluene feed prepared in Example 3 from 1-pentene and toluene was reformed on the sulfided Pt—Re/Al$_2$O$_3$/Cl catalyst of Example 7 at 950° F., 50 psig, molar H$_2$-to-pentyltoluenes ratio of about 6:1 and three different WHSV's: 1,3 and 6 h$^{-1}$. The on-line GC analysis results collected at various reaction times are shown in Table 5. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. The results show that higher WHSV of the pentyltoluene feed resulted in lower DMN yield and higher catalyst deactivation rate.

TABLE 5

Reforming of Pentyltoluenes on Pt-Re/Al$_2$O$_3$/Cl under Various WHSV (950° F. and 50 psig)

| | WHSV, h$^{-1}$ | | | | | |
|---|---|---|---|---|---|---|
| | 1 | | 3 | | 6 | |
| Reaction Time, h | 3 | 63 | 3 | 64 | 3 | 19 |
| PT Conversion, % | 100 | 86 | 100 | 55 | 77 | 34 |
| DMN Yield, % | | | | | | |
| 1,5-DMN | 4.8 | 4.5 | 6.1 | 1.6 | 4.2 | 0.5 |
| 1,6-DMN | 20.2 | 14.3 | 19.3 | 6.1 | 12.7 | 1.9 |
| 1,7-DMN | 16.9 | 14.1 | 18.5 | 6.0 | 13.2 | 1.9 |
| 2,6/2,7-DMN | 33.2 | 15.5 | 22.1 | 5.9 | 13.0 | 2.0 |
| Total DMN's | 75.1 | 48.4 | 66.0 | 19.6 | 43.1 | 6.3 |
| DMN Selectivity, % | 75.1 | 56.2 | 66.0 | 35.6 | 56 | 18.5 |

EXAMPLE 13

Pentyltoluene Reforming on Pt—Re/Al$_2$O$_3$/Cl Catalyst at Various Weight Hourly Space Velocities The pentyltoluene feed prepared in Example 3 from 1-pentene and toluene was reformed on the sulfided Pt—Re/Al$_2$O$_3$/Cl catalyst of Example 7 at 950° F., ~5 psig, molar H$_2$-to-pentyltoluenes ratio of about 6:1, and three different WHSV's: 1,0.5 and 0.25 h$^{-1}$. The results are shown in Table 6 in terms of pentyltoluene conversion, DMN yield and DMN selectivity versus reaction time, respectively. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. The results show that lower WHSV of the pentyltoluene feed improved the catalyst stability.

TABLE 6

Conversion of Pentyltoluenes on Pt-Re/Al$_2$O$_3$/Cl under Various WHSV (950° F. and ~5 psig)

| | WHSV, h$^{-1}$ | | | | | | | | |
|---|---|---|---|---|---|---|---|---|---|
| | 1 | | | 0.5 | | | 0.25 | | |
| Reaction Time, h | 4 | 15 | 70 | 4 | 15 | 70 | 4 | 15 | 70 |
| PT Conversion, % | 100 | 72 | — | 100 | 95 | 76 | 100 | 99 | 82 |
| DMN Yield, % | | | | | | | | | |
| 1,5-DMN | 6.9 | 2.5 | — | 4.9 | 5.2 | 2.7 | 4.3 | 4.5 | 3.4 |
| 1,6-DMN | 19.8 | 9.5 | — | 18.5 | 16.9 | 10.7 | 17.0 | 16.9 | 13.6 |
| 1,7-DMN | 23.8 | 9.9 | — | 20.3 | 20.3 | 11.1 | 19.6 | 19.0 | 13.7 |
| 2,6/2,7-DMN | 32.2 | 13.2 | — | 35.8 | 29.6 | 14.9 | 35.2 | 33.2 | 22.0 |
| Total DMN's | 82.7 | 35.1 | — | 79.5 | 72.0 | 39.4 | 76.1 | 73.6 | 52.7 |
| DMN Selectivity, % | 82.7 | 48.8 | — | 79.5 | 75.8 | 40.4 | 76.1 | 74.3 | 64.3 |

EXAMPLE 14

Pentyltoluene Reforming on Pt—Re/Al$_2$O$_3$/Cl Catalyst at Various Pressures

The pentyltoluene feed prepared in Example 3 from 1-pentene and toluene was reformed on the sulfided Pt—Re/Al$_2$O$_3$/Cl catalyst of Example 7 at 950° F., 1 h$^{-1}$ WHSV, molar H$_2$-to-pentyltoluenes ratio of about 6:1, and two different pressures: ~5 and 50 psig. The results obtained under these two sets of conditions are shown in Table 5 (Example 12) and Table 6 (Example 13), respectively, in terms of pentyltoluene conversion, DMN yield and DMN selectivity versus reaction time, respectively. The results show that relatively higher pressure improved the catalyst stability.

EXAMPLE 15

Pentyltoluene Reforming on Pt—Re/Al$_2$O$_3$/Cl Catalyst under Various Conditions The pentyltoluene feed prepared in Example 3 from 1-pentene and toluene was reformed on the sulfided Pt—Re/Al$_2$O$_3$/Cl catalyst of Example 7 at 870° F., 0.17 h$^{-1}$ WHSV, a molar H$_2$-to-pentyltoluenes ratio of about 6:1, and two different pressures: first, 100 psig (0–90 hours) and then 50 psig (90–240 hours). The experiment was conducted for about 240 hours without interruption. The results are shown Table 7 in terms of DMN yield versus reaction time. The pentyltoluene conversion was about 100% during the entire experiment. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethyinaphthalenes (EN) was formed. The off-line GC analysis showed that the ratio of 2,6/2,7-DMN was about 1:1. The results show that lower pressure improved the DMN yield. The experiment demonstrated also an unusually stable catalyst performance under these conditions.

TABLE 7

DMN Selectivity on Pt-Re/Al$_2$O$_3$/Cl under Various Conditions

| Reaction Time, h | 41 | 71 | 89 | 101 | 173 | 236 |
|---|---|---|---|---|---|---|
| Pressure, psig | | 100 | | | 50 | |
| DMN Yield, % | | | | | | |
| 1,5-DMN | 0.9 | 1.0 | 1.0 | 1.9 | 2.0 | 2.1 |
| 1,6-DMN | 5.2 | 5.4 | 5.4 | 9.9 | 10.5 | 10.6 |
| 1,7-DMN | 4.5 | 4.6 | 4.8 | 8.4 | 8.6 | 8.5 |
| 2,6/2,7-DMN | 9.7 | 10.2 | 10.5 | 18.4 | 19.2 | 18.9 |
| Total DMN's | 20.3 | 21.2 | 21.7 | 38.6 | 40.3 | 40.1 |

EXAMPLE 16

Reforming of Pentyltoluenes Prepared from Different C$_5$ Olefin Sources

This example compares the catalytic performance of the sulfided Pt—Re/Al$_2$O$_3$/Cl catalyst of Example 7 for reforming of pentyltoluene feeds prepared from toluene alkylation with C$_5$ olefins of various sources: (1) 1-pentene (Example 3), (2) TAME Raffinate (Example 5) and (3) FCC C$_5$'s (Example 6).

The reaction conditions were as follows: 950° F., 50 psig, molar H$_2$:PT ratio of ~6:1, and WHSV of 1 h$^{-1}$. The on-line GC analysis results collected at ~3 hours of reaction time are shown in Table 8. The conversion of pentyltoluene feed was ~100%. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethnylnaphthalenes (EN) was formed. The off-line GC analysis showed that the ratio of 2,6/2,7-DMN was about 1:1.

TABLE 8

Reforming of Pentyltoluenes Prepared from Toluene Alkylation with C$_5$ Olefin(s) of Different Sources

| | C$_5$olefin source | | |
|---|---|---|---|
| DMN yield, % | 1-pentene | TAME Raffinate | FCC C$_5$'s |
| 1,5-DMN | 4.8 | 4.0 | 2.0 |
| 1,6-DMN | 20.2 | 13.5 | 14.0 |

TABLE 8-continued

Reforming of Pentyltoluenes Prepared from
Toluene Alkylation with C₅ Olefin(s) of Different Sources

| | C₅ olefin source | | |
|---|---|---|---|
| DMN yield, % | 1-pentene | TAME Raffinate | FCC C₅'s |
| 1,7-DMN | 16.9 | 20.5 | 8.7 |
| 2,6/2,7-DMN | 33.2 | 32.1 | 20.1 |
| Total DMN's | 75.1 | 70.1 | 44.8 |

EXAMPLE 17

Pentyltoluene Reforming on Pt—Re/Al$_2$O$_3$/Cl Catalyst without Diluent/Co-feed The pentyltoluene feed prepared in Example 6 from FCC C$_5$'s and toluene was reformed on the sulfided Pt—Re/Al$_2$O$_3$/Cl of Example 7 at 870° F., 50 psig, 0.17 h$^{-1}$ WHSV, and molar H$_2$-to-pentyltoluenes ratio of about 6:1. The results are shown in Table 9 in terms of DMN yield versus reaction time. The pentyltoluene conversion was ~100% during this experiment. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. The results when compared with the results of Example 15 (Table 7) show that DMN yield was lowered when the pentyltoluene feed made from FCC C$_5$'s was used instead of the pentyltoluene feed made from 1-pentene (also see Example 16, Table 8).

identical to those reported in Examples 17, 19 and 20. The results are shown in Table 9 in terms of DMN yield versus reaction time, together with the results obtained in Examples 17, 19 and 20. The pentyltoluene conversion was ~100% during this experiment. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. Compared to the results from Example 17 (without diluent under otherwise identical conditions), the diluting of pentyltoluenes with benzene significantly improved the DMN yield.

In addition, the results from a reference experiment using pure benzene as feed under otherwise identical conditions indicated that benzene essentially didn't undergo any chemical reactions (data not shown).

EXAMPLE 19

Pentyltoluene Reforming on Pt—Re/Al$_2$O$_3$/Cl Catalyst in the Presence of Toluene as Diluent The pentyltoluene feed prepared in Example 6 from FCC C$_5$'s and toluene was reformed on the sulfided Pt—Re/Al$_2$O$_3$/Cl catalyst of Example 7 at 870° F. and 50 psig in the presence of toluene as diluent. In this case, the pentyltoluene (PT) feed was blended with toluene at a weight ratio of PT to toluene of 1:2 and the molar H$_2$-to-pentyltoluenes ratio was about 6:1. The WHSV of pentyltoluenes wets still kept to 0.17 h$^{-1}$. The reaction conditions were otherwise identical to those reported in Examples 17, 18 and 20. The results are shown in Table 9 in terms of DMN yield versus reaction time, together with the results obtained in Examples 17, 18

TABLE 9

DMN Selectivity on Pt-Re/Al$_2$O$_3$/Cl with/without Diluent/Co-feed

| | Example | | | | | | | | | | | |
|---|---|---|---|---|---|---|---|---|---|---|---|---|
| | 17 | | | 18 | | | 19 | | | 20 | | |
| | | | | | | Diluent/Co-feed | | | | | | |
| | None | | | Benzene | | | Toluene | | | C$_7$ naphtha | | |
| Reaction Time, h | 5 | 29 | 70 | 5 | 30 | 70 | 5 | 33 | 69 | 5 | 31 | 71 |
| DMN Yield*, % | | | | | | | | | | | | |
| 1,5-DMN | 1.2 | 1.3 | 1.1 | 1.8 | 2.1 | 2.0 | 1.8 | 2.3 | 2.3 | 2.0 | 2.3 | 2.4 |
| 1,6-DMN | 6.0 | 6.7 | 5.7 | 9.0 | 10.4 | 9.7 | 9.0 | 10.9 | 10.5 | 9.6 | 10.6 | 10.4 |
| 1,7-DMN | 5.4 | 5.9 | 5.0 | 7.8 | 8.7 | 8.1 | 7.6 | 9.2 | 8.9 | 8.3 | 9.1 | 9.1 |
| 2,6/2,7-DMN | 14.1 | 14.7 | 12.6 | 16.9 | 19.0 | 17.5 | 16.7 | 19.5 | 18.5 | 18.3 | 19.4 | 18.4 |
| Total DMN's | 26.7 | 28.6 | 24.4 | 35.5 | 40.2 | 37.3 | 35.1 | 41.9 | 40.2 | 38.2 | 41.4 | 40.3 |

*DMN yield reported based on pentyltoluene feed, not total hydrocarbon feed.

EXAMPLE 18

Pentyltoluene Reforming on Pt—Re/Al$_2$O$_3$/Cl Catalyst in the Presence of Benzene as Diluent The pentyltoluene feed prepared in Example 6 from FCC C$_5$'s and toluene was reformed on the sulfided Pt—Re/Al$_2$O$_3$/Cl catalyst of Example 7 at 870° F. and 50 psig in the presence of benzene as diluent. In this case, the pentyltoluene (PT) feed was blended with benzene at a weight ratio of PT to benzene of 1:2 and the molar H$_2$-to-pentyltoluenes ratio was about 6:1. The WHSV of pentyltoluenes was still kept to 0.17 h$^{-1}$. The reaction conditions were otherwise and 20. The pentyltoluene conversion was ~100% during this experiment. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. Compared to the results from Example 17 (without diluent under otherwise identical conditions), the diluting of pentyltoluenes with toluene significantly improved the DMN yield, which was similar to the results from Example 18 with benzene as diluent.

In addition, the results from a reference experiment using pure toluene as feed under otherwise identical conditions indicated that toluene only slightly underwent some chemical reactions (mainly <2% benzene detected) (data not shown).

EXAMPLE 20

Pentyltoluene Reforming on Pt—Re/$Al_2O_3$/Cl Catalyst in the Presence of a $C_7$ Naphtha as Co-Feed The pentyltoluene feed prepared in Example 6 from FCC $C_5$'s and toluene was reformed on the sulfided Pt—Re/$Al_2O_3$/Cl catalyst of Example 7 at 870° F. and 50 psig in the presence of a $C_7$ naphtha as co-feed. The composition of this $C_7$ naphtha co-feed is shown in Table 10. In this case, the pentyltoluene (PT) feed was blended with this $C_7$ naphtha at a weight ratio of PT to $C_7$'s of 1:2 and the molar $H_2$-to-pentyltoluenes ratio was about 6:1. The WHSV of pentyltoluenes was still kept to 0.17 $h^{-1}$. The reaction conditions were otherwise identical to those reported in Examples 17–19. The results are shown in Table 9 in terms of DMN yield versus reaction time, together with the results obtained in Examples 17–19. The pentyltoluene conversion was ~100% during this experiment. The resulting DMN's were essentially only those DMN isomers which have the two methyl groups on different aromatic rings, namely, 1,5-DMN, 1,6-DMN, 1,7-DMN, 2,6-DMN and 2,7-DMN. Only a very small amount of ethylnaphthalenes (EN) was formed. The off-line GC analysis showed that the ratio of 2,6/2,7-DMN was about 1:1. Compared to the results from Example 17 (without co-feed under otherwise identical conditions), the co-feeding of pentyltoluenes with $C_7$ naphtha significantly improved the DMN yield, which was similar to the results from Examples 18 and 19 with benzene and toluene as diluents, respectively.

TABLE 10

Composition of the $C_7$ Naphtha

| Composition: | wt. % |
| --- | --- |
| 3,3,-dimethylpentane | 0.72 |
| Cyclohexane | 0.64 |
| 2-methylhexane | 20.63 |
| 2,3-dimethylpentane | 8.76 |
| 1,1-dimethylcyclopentane | 5.75 |
| 3-methylhexane | 20.49 |
| cis-1,3-dimethylcyclopentane | 10.0 |
| trans-1,2-dimethylcyclopentane | 9.14 |
| trans-1,3-dimethylcyclopentane | 13.24 |
| n-heptane | 7.98 |
| Methylcyclohexane | 2.33 |
| Ethylcyclopentane | 0.05 |

The toluene yield obtained from the experimental run of this example was about 32%. The resulting toluene consisted of the contributions of both $C_7$ reforming and pentyltoluene dealkylation. The toluene yield can be adjusted by adjusting the PT-to-$C_7$ ratio in the reforming feed.

When the $C_7$ naphtha was co-fed, toluene was the major reforming product from this co-feed. The advantage of using this kind of co-feed is that its reforming product toluene can be used then within the integrated DMN process for toluene alkylation with $C_5$ olefins in the alkylation step. It means that it may only need a $C_7$ or $C_6$–$C_{12}$ naphtha stream for co-reforming to make toluene and no extra toluene feed stream may be required. The integrated process of this invention may require, therefore, only (1) a $C_7$ or $C_6$–$C_{12}$ naphtha stream (to make toluene) and (2) $C_5$ olefins (to alkylate the resulting toluene for making pentyltoluenes which will be then reformed to DMN's with toluene as major dealkylation product).

What is claimed is:

1. A method of making DMN, the method comprising:
    a. contacting in an alkylation zone, at a temperature of from about 32° F. to about 500° F. and a pressure of from about ambient to about 500 psig, a toluene-containing stream with a TAME raffinate stream, wherein the molar ratio of toluene in said toluene-containing stream to pentenes in said TAME raffinate stream is from about 4:1 to about 12:1; and the WHSV of said toluene-containing stream and said TAME raffinate stream combined is from about 1 $h^{-1}$ to about 8 $h^{-1}$, wherein said contacting is in the presence of an acid alkylation catalyst selected from the group consisting of aluminum chloride, acid clays, heteropolyacids, acidic zeolites having a pore diameter of at least about 4.5 angstroms, solid phosphoric acid catalysts, and mixtures thereof, wherein at least a portion of said toluene and said TAME raffinate react to form pentyltoluenes;
    b. recovering from said alkylation zone at least a portion of said pentyltoluenes;
    c. passing a $C_7$ naphtha-containing stream and at least a portion of said pentyltoluenes to a reforming zone containing an amorphous platinum/alumina reforming catalyst comprising a metal selected from the group consisting of a non-platinum Group VIIIB metal, rhenium, germanium, tin, lead, gallium, indium, and mixtures thereof;
    d. contacting in said reforming zone, said $C_7$ naphtha-containing stream and said pentyltoluenes and said reforming catalyst, under reforming conditions comprising a pressure from about ambient to about 500 psig, a temperature from about 700° F. to about 1000° F., the molar ratio of hydrogen to $C_7$ naphtha-containing stream and pentyltoluenes combined is from about 1:1 to about 15:1, the pentyltoluenes WHSV is from about 0.1 $h^{-1}$ to about 10 $h^{-1}$, and the $C_7$ naphtha to pentyltoluenes weight ratio is from about 0:1 to about 1000:1, wherein:
        (i) at least a portion of said pentyltoluenes is converted to DMN's; and
        (ii) at least a portion of said $C_7$ naphtha is converted to toluene;
    e. recovering from said reforming zone at least a portion of said DMN's; and
    f. passing at least a portion of said toluene produced in step (d) to said alkylation zone in step (a).

2. A method of making DMN's, comprising contacting in a reforming zone a pentyltoluenes containing feed with a platinum-containing amorphous reforming catalyst, further comprising a metal selected from the group consisting of a non-platinum Group VIIIB metal, rhenium, germanium, tin, lead, gallium, indium, and mixtures thereof, at reforming conditions, wherein at least a portion of said pentyltoluenes is converted to DMN's.

3. The method of claim 2 wherein said reforming catalyst further comprises a support selected from the group consisting of alumina, silica, titania, vanadia, chromia, zirconia, and mixtures thereof.

4. The method of claim 2 wherein said reforming catalyst further comprises an alumina support.

5. The method of claim 2 wherein said reforming catalyst further comprises a support selected from the group consisting of silica, titania, vanadia, chromia, zirconia, and mixtures thereof.

6. The method of claim 2 wherein said reforming catalyst further comprises rhenium.

7. The method of claim 2 wherein said reforming catalyst further comprises germanium.

8. The method of claim 2 wherein said reforming catalyst further comprises tin.

9. The method of claim 2 further comprising separating said DMN's from any unreacted pentyltoluenes and recycling at least a portion of said unreacted pentyltoluenes to said reforming zone.

10. The method of claim 2 wherein said reforming conditions comprise a pressure from about ambient to about 500 psig.

11. The method of claim 2 wherein said reforming conditions comprise a pressure from about ambient to about 300 psig.

12. The method of claim 2 wherein said reforming conditions comprise a temperature from about 700° F. to about 1000° F.

13. The method of claim 2 wherein said reforming conditions comprise a pentyltoluenes WHSV of from about 0.01 $h^{-1}$ to about 100 $h^{-1}$.

14. The method of claim 2 wherein said reforming conditions comprise a pentyltoluenes WHSV of from about 0.1 $h^{-1}$ to about 10 $h^{-1}$ and the molar ratio of hydrogen to pentyltoluenes is from about 1:1 to about 15:1.

15. The method of claim 2, further comprising:
   a. contacting, in an alkylation zone, at alkylation conditions, a toluene-containing stream with a $C_5$ olefin containing stream in the presence of an acid alkylation catalyst, wherein at least a portion of said toluene and said $C_5$ olefins react to form pentyltoluenes; and
   b. passing at least a portion of said pentyltoluenes to said reforming zone.

16. The method of claim 15 wherein said $C_5$ olefin containing stream comprises a TAME raffinate.

17. The method of claim 15 wherein said $C_5$ olefin containing stream comprises an FCC $C_5$ stream.

18. The method of claim 15 wherein said alkylation conditions comprise a pressure of from about ambient to about 500 psig, a temperature from about 32° F. to about 500° F., a toluene to $C_5$ olefin molar ratio of from about 4:1 to about 12:1, and a WHSV of from about 1 $h^{-1}$ to about 8 $h^{-1}$.

19. The method of claim 15 wherein said alkylation catalyst is a Y-zeolite and said alkylation conditions comprise a temperature of from about 100° F. to about 400° F., a pressure from about ambient to about 300 psig.

20. The method of claim 15 wherein said alkylation catalyst is $AlCl_3$ and said alkylation conditions comprise a temperature of from about 32° F. to about 300° F., a pressure from about ambient to about 300 psig.

21. The method of claim 15 wherein said acid alkylation catalyst is selected from the group consisting of aluminum chloride, acid clays, solid phosphoric acid catalysts, heteropolyacids, acidic zeolites having a pore diameter of at least about 4.5 angstroms, and mixtures thereof.

22. The method of claim 15 wherein said acid alkylation catalyst is selected from the group consisting of Y zeolite, beta zeolite, mordenite, offretite, omega, ferrierite, SSZ-20, SSZ-24, SSZ-25, SSZ-26, SSZ-31, SSZ-32, SSZ-33, SSZ-35, SSZ-37, SSZ-42, SSZ-44, EU-1, NU-86, NU-87, UTD-1, ZSM-5, ZSM-11, ZSM-12, ZSM-35, ZSM-48, MCM-22, MCM-36, MCM-56, and mixtures thereof.

23. The method of claim 2 further comprising passing a diluent to said reforming zone.

24. The method of claim 2 wherein said diluent is selected from the group consisting of benzene, toluene, xylenes, $C_5$ naphtha, and mixtures thereof.

25. The method of claim 2 wherein the weight ratio of said diluent to said pentyltoluenes containing feed is from about 0:1 to about 1000:1.

26. The method of claim 2 further comprising co-feeding a $C_6$–$C_{12}$ naphtha-containing stream to said reforming zone.

27. The method of claim 2 wherein the weight ratio of said co-feed to said pentyltoluenes containing feed is from about 0:1 to about 1000:1.

28. A method of making DMN's, the method comprising:
   a. passing a $C_6$–$C_{12}$ naphtha-containing stream and a pentyltoluenes-containing stream to a reforming zone containing an amorphous platinum/alumina reforming catalyst; and
   b. contacting in said reforming zone, said $C_6$–$C_{12}$ naphtha-containing stream and said pentyltoluenes and said reforming catalyst, under reforming conditions, wherein:
      (i) at least a portion of said pentyltoluenes is converted to DMN's; and
      (ii) at least a portion of said $C_6$–$C_{12}$ naphtha is converted to aromatics.

29. The method of claim 28 wherein said $C_6$–$C_{12}$ naphtha consists essentially of a $C_7$ naphtha and where at least a portion of said $C_7$ naphtha is converted to toluene, and further comprising passing at least a portion of said toluene to an alkylation zone.

30. The method of claim 28 wherein said reforming catalyst further comprises a metal selected from the group consisting of a non-platinum Group VIIIB metal, rhenium, germanium, tin, lead, gallium, indium, and mixtures thereof.

31. The method of claim 28 wherein said reforming catalyst further comprises rhenium.

32. The method of claim 28 wherein said reforming catalyst further comprises germanium.

33. The method of claim 28 wherein said reforming catalyst further comprises tin.

34. The method of claim 28 further comprising separating said DMN's from any unreacted pentyltoluenes and recycling at least a portion of said unreacted pentyltoluenes to said reforming zone.

35. The method of claim 28 wherein said reforming conditions comprise a pressure from about ambient to about 500 psi.

36. The method of claim 28 wherein said reforming conditions comprise a temperature from about 700° F. to about 1000° F.

37. The method of claim 28 wherein said reforming conditions comprise a pentyltoluenes WHSV of from about 0.01 $h^{-1}$ to about 100 $h^{-1}$.

38. The method of claim 28 wherein said reforming conditions comprise a pentyltoluenes WHSV of from about 0.1 $h^{-1}$ to about 10 $h^{-1}$, the molar ratio of hydrogen to $C_6$–$C_{12}$ naphtha-containing stream and pentyltoluenes combined is from about 1:1 to about 15:1, and the weight ratio of the $C_6$–$C_{12}$ naphtha-containing stream to pentyltoluenes is from about 0:1 to about 1000:1.

39. The method of claim 29, further comprising:
   a. contacting, in said alkylation zone, at alkylation conditions, a toluene-containing stream with a $C_5$ olefin containing stream in the presence of an acid alkylation catalyst, wherein at least a portion of said toluene and said $C_5$ olefins react to form pentyltoluenes; and
   b. passing at least a portion of said pentyltoluenes to said reforming zone.

40. The method of claim 39 wherein said $C_5$ olefin containing stream comprises a TAME raffinate.

41. The method of claim 39 wherein said $C_5$ olefin containing stream comprises an FCC $C_5$ stream.

42. The method of claim 39 wherein said alkylation conditions comprise a pressure of from about ambient to about 500 psig, a toluene to $C_5$ olefin molar ratio of from about 4:1 to about 12:1, and a WHSV of from about 1 $h^{-1}$ to about 8 $h^{-1}$, and a temperature from about 32° F. to about 500° F.

43. The method of claim 39 wherein said alkylation catalyst is a Y-zeolite and said alkylation conditions comprise a temperature of from about 100° F. to about 400° F., and a pressure from about ambient to about 300 psig.

44. The method of claim 39 wherein said alkylation catalyst is $AlCl_3$ and said alkylation conditions comprise a temperature of from about 32° F. to about 300° F., and a pressure from about ambient to about 300 psig.

45. The method of claim 39 wherein said acid alkylation catalyst is selected from the group consisting of aluminum chloride, acid clays, solid phosphoric acid catalysts, heteropolyacids, acidic zeolites having a pore diameter of at least about 4.5 angstroms, and mixtures thereof.

46. The method of claim 39 wherein said acid alkylation catalyst is selected from the group consisting of Y zeolite, beta zeolite, mordenite, offretite, omega, ferrierite, SSZ-20, SSZ-24, SSZ-25, SSZ-26, SSZ-31, SSZ-32, SSZ-33, SSZ-35, SSZ-37, SSZ-42, SSZ-44, EU-1, NU-86, NU-87, UTD-1, ZSM-5, ZSM-11, ZSM-12, ZSM-35, ZSM-48, MCM-22, MCM-36, MCM-56, and mixtures thereof.

47. The method of claim 28 further comprising passing a diluent to said reforming zone.

48. The method of claim 47 wherein said diluent is selected from the group consisting of benzene, toluene, xylenes, $C_5$ naphtha, and mixtures thereof.

49. The method of claim 47 wherein the weight ratio of said diluent to said pentyltoluenes containing feed is from about 0:1 to about 1000:1.

50. The method of claim 28 wherein the weight ratio of said $C_6$–$C_{12}$ naphtha-containing stream to said pentyltoluenes containing feed is from about 0:1 to about 1000:1.

* * * * *